(12) United States Patent
Lane (10) Patent No.: US 7,956,045 B2
(45) Date of Patent: Jun. 7, 2011

(54) COMPOSITIONS AND METHODS FOR ANIMAL TREATMENT

(75) Inventor: Rowan L. Lane, Auckland (NZ)

(73) Assignee: Vitalan Limited, Auckland (NZ)

( * ) Notice: Subject to any disclaimer, the term of this patent is extended or adjusted under 35 U.S.C. 154(b) by 790 days.

(21) Appl. No.: 10/497,291

(22) PCT Filed: Dec. 2, 2002

(86) PCT No.: PCT/NZ02/00268
§ 371 (c)(1),
(2), (4) Date: Nov. 16, 2004

(87) PCT Pub. No.: WO03/045401
PCT Pub. Date: Jun. 5, 2003

(65) Prior Publication Data
US 2005/0075311 A1    Apr. 7, 2005

(30) Foreign Application Priority Data
Nov. 30, 2001    (NZ) ........................ 515869

(51) Int. Cl.
*A61K 31/715* (2006.01)
(52) U.S. Cl. ............ 514/54; 514/61; 514/23; 536/123.1
(58) Field of Classification Search ............. 514/54, 514/61, 23; 536/123.1
See application file for complete search history.

(56) References Cited

U.S. PATENT DOCUMENTS

| | | |
|---|---|---|
| 4,793,229 A | 12/1988 | Kleber |
| 4,873,229 A | 10/1989 | Deya et al. |
| 5,518,733 A | 5/1996 | Lamothe et al. |
| 5,962,423 A | 10/1999 | Bundle et al. |
| 5,972,905 A | 10/1999 | Hosokawa et al. |
| 6,451,584 B2 | 9/2002 | Tomita et al. |
| 6,630,586 B1 | 10/2003 | Fouache et al. |

FOREIGN PATENT DOCUMENTS

| | | |
|---|---|---|
| EP | 0 171 026 | 10/1991 |
| EP | 0 293 935 | 9/1992 |
| EP | 0 549 478 | 9/1992 |
| EP | 1 006 128 | 6/2000 |
| EP | 1 072 268 | 1/2001 |
| JP | 3-27255 | 2/1991 |
| JP | 03031294 A * | 2/1991 |
| JP | 08023889 A * | 1/1996 |
| WO | WO-89/03218 | 4/1989 |
| WO | WO-97/34615 | 9/1997 |

OTHER PUBLICATIONS

Hirooka et al. (JP 03031294 A.), Feb. 2, 1991 (Abstract Sent).*
Unno et al. (Denpun Kagaku (1993), 40(1), 21-7) (Abstract sent).*
Gabert et al. (Schriftenreihe-Forschungsinstitut fuer die Biologie Landwirtschaftlicher Nutztiere (1994), 4 (VIth International Symposium on Digestive Physiology in Pigs, 1994, vol. 2), 259-262) (Abstract sent).*
Kurokawa et al; JP 08023889 A, Jan. 30, 1996 (Abstract sent).*
Nakai et al. (JP 10099040 A, Apr. 21, 1998 (Abstract sent).*
Monsan et al. (oligosaccharide feed additives. In: Biotechnology in Animal Feeds and Feeding, Wallace, R.C.; Chesson, A.; eds, VCH, Weinheim, 1995, pp. 233-245).*
Unno, et al: "Effect of β-Glucooligosaccharides on the Human Intestinal Microflora".
Translation of Japanese Application Publication No. TOKUKAIHEI8-23889 along with Statement of Accuracy signed by translator Nobuko Delowe, Jan. 30, 1996.
Translation of Japanese Patent Application Publication No. TOKUKAIHEI0-99040 along with Statement of Accuracy signed by translator Nobuko Delowe, Apr. 21, 1998.

* cited by examiner

*Primary Examiner* — Anna Jiang
*Assistant Examiner* — Michael C Henry
(74) *Attorney, Agent, or Firm* — Edwards Angell Palmer & Dodge LLP; Jeffrey D. Hsi (57) ABSTRACT

A method of improving the health and production of ruminant animals, the method including the step of orally administering to the animal an effective amount of an indigestible oligosaccharide selected from the group of gluco-oligosaccharides and isomalto-oligosaccharides.

14 Claims, 4 Drawing Sheets

COMPOSITIONS AND METHODS FOR ANIMAL TREATMENT

FIELD OF THE INVENTION

The invention relates to the use of indigestible oligosaccharides to improve the health and productivity of ruminant animals and to an oligosaccharide composition of use in such a method. In one aspect in particular the invention relates to the use of gluco- and/or isomalto-oligosaccharides to treat/control infective diarrhea in ruminant animals and to a composition of use in that treatment/control. Further, in another aspect the invention relates to a method of increasing lactation in animals, and in particular adult bovine animals, via the use of gluco- and/or isomalto-oligosaccharides and to a composition of use in such a method.

BACKGROUND

Bacterial and viral infection of the digestive tract in newborn and adult animals, resulting in the onset of infective diarrhea, is a significant cause of animal fatality, animal health risk and cross infection to the human population. There is a significant economic impact on the agricultural sector from reduced natural production and disease and health control costs. Traditional methods of dealing with these infections include the use of antibiotic preparations and remedial electrolyte compounds that are administered as injectable or oral drenching solutions. Such methods can be expensive and can be difficult to administer, particularly for animals grazed in remote pastures. In addition, there is a move away, in some sectors of the agricultural community, from antibiotic use to more natural, non-invasive, treatment methods.

There is also a desire to maximize milk production, in dairy herds in particular, in order to maximize economic returns to the farmer. Therefore the ability to assist in increasing milk production would also be a desirable aim.

The ability to provide an alternative method of improving the health and production of ruminant animals and/or compositions of use in such a method will have a clear economic benefit to the farming community.

OBJECT OF THE INVENTION

It is one object of the invention to assist in the improvement of the health and production of ruminant animals.

It is an alternative object to assist in increasing milk production in lactating ruminant animals and/or to assist in the treatment/control of infective diarrhea in ruminant animals.

SUMMARY OF THE INVENTION

According to one aspect of the present invention, there is provided a method of improving the health and production of ruminant animals, the method including the step of orally administering to the animal an effective amount of an indigestible oligosaccharide selected from the group of gluco-oligosaccharides and isomalto-oligosaccharides.

Preferably the method decreases the incidence of infective diarrhea in ruminant animals.

Preferably the method increases milk production in lactating ruminant animals.

Preferably the indigestible oligosaccharide is carried in a nutritional support product such as milk, reconstituted milk, milk replacer, water, fortified water, electrolyte solutions, water gels or blended powders.

Preferably the ruminant animal is a bovine, ovine or cervine animal.

Preferably the nutritional support product contains conventional additives and/or excipients including inorganic mineral salts, vitamins, attractants and other additives.

Preferably the nutritional support product is a water gel system.

Preferably the water gel system is thermostable.

Preferably the thermostable water gel system is able to withstand an extended period of residence in the rumen gut.

Preferably the amount of indigestible oligosaccharide is administered to the animal at a daily rate of between about 2-60 grams.

Preferably the amount of indigestible oligosaccharide is administered to the animal at a daily rate of between about 5-30 grams.

Preferably the amount of indigestible oligosaccharide is administered to the animal at a daily rate of between about 10-30 grams for bovine animals and about 2-20 grams for ovine animals.

Preferably the amount of indigestible oligosaccharide is administered to the animal at a daily rate of between about 15-25 grams for bovine animals and about 5-10 grams for ovine animals.

Preferably the indigestible oligosaccharide is present in the nutritional support product in an amount of between about 150 and 5000 ppm, more preferably between about 300 and 5000 ppm and more preferably between about 300 and 1000 ppm.

Preferably the method treats infective diarrhea caused by *E. coli*, ETEC, EPEC, EHEC, EIEC, *Salmonella, Salmonella* Brandenburg, *Listeria monocytogenes, Clostridium perfringens. Campylobacter, Staphylococcus aureus, Streptococcus, Rotavirus, Coronavirus, Cryptosporidia*.

Preferably the method treats infective diarrhea caused by *E coli* and/or *Salmonella* Brandenburg.

According to a further aspect of the invention there is provided a method of Increasing milk production in bovine animals including the step of orally administering to the bovine animal a composition containing an effective amount of a gluco- and/or isomalto-oligosaccharide.

Preferably the composition used also includes a nutritional support product.

Preferably the nutritional support product is selected from milk, reconstituted milk, milk replacer, water, fortified water, electrolyte solutions, water gels or blended powders.

Preferably the nutritional support product is a water gel system.

Preferably the water gel system is thermostable.

Preferably the thermostable water gel system is able to withstand an extended period of residence in the rumen gut.

Preferably the amount of gluco-oligosaccharide and/or isomalto-oligosaccharide is administered to the animal a daily rate of between about 2-60 grams.

Preferably the amount of gluco-oligosaccharide and/or isomalto-oligosaccharide is administered at to the animal a daily rate of between about 5-30 grams.

Preferably the amount of gluco-oligosaccharide and/or isomalto-oligosaccharide is administered at a daily rate of between about 10-30 grams.

Preferably the amount of gluco-oligosaccharide and/or isomalto-oligosaccharide is administered at a daily rate of between about 15-25 grams.

Preferably the gluco-oligosaccharide and/or isomalto-oligosaccharide is present in the composition in an amount of between about 150 and 5000 ppm, more preferably between about 300 and 5000 ppm and more preferably between about 300 and 1000 ppm.

According to another aspect of the invention there is provided a method of treating/combating infective diarrhea in ruminant animals including the step of orally administering to the ruminant animal a composition containing an effective amount of a gluco- and/or isomalto-oligosaccharide.

Preferably the composition also includes a nutritional support product.

Preferably the nutritional support product is selected from milk, reconstituted milk, milk replacer, water, fortified water, electrolyte solutions, water gels or blended powders.

Preferably the nutritional support product is a water gel system.

Preferably the water gel system is thermostable.

Preferably the thermostable water gel system is able to withstand an extended period of residence in the rumen gut.

Preferably the amount of indigestible oligosaccharide is administered to the animal at a daily rate of between about 2-60 grams.

Preferably the amount of indigestible oligosaccharide is administered to the animal at a daily rate of between about 5-30 grams.

Preferably the amount of indigestible oligosaccharide is administered to the animal at a daily rate of between about 10-30 grams in bovine animals and about 2-20 grams for ovine animals.

Preferably the amount of indigestible oligosaccharide is administered to the animal at a daily rate of between about 15-25 grams in bovine animals and about 5-10 grams for ovine animals.

Preferably the indigestible oligosaccharide is present in the composition in an amount of between about 150 and 5000 ppm, more preferably between about 300 and 5000 ppm and more preferably between about 300 and 1000 ppm.

Preferably the method treats infective diarrhea caused by *E coli*, ETEC, EPEC, EHEC, EIEC, *Salmonella, Salmonella* Brandenburg, *Listeria monocytogenes, Clostridium perfringens, Campylobacter, Staphylococcus aureus, Streptococcus, Rotavirus, Coronavirus, Cryptosporidia*.

Preferably the method treats infective diarrhea caused by *E. coli* and/or *Salmonella* Brandenburg.

According to another aspect of the invention there is provided a composition for increasing milk production in lactating animals and/or treating/controlling infective diarrhea, the composition including a nutritional support product and between about 150 and 5000 ppm of gluco- and/or isomalto-oligosaccharides.

Preferably the gluco and/or isomalto oligosaccharide is present in an amount of between about 300 and 5000 ppm or, more preferably between about 300 and 1000 ppm.

Preferably the nutritional support product is a product such as milk, reconstituted milk, milk replacer, water, fortified water, electrolyte solutions, water gels or blended powders.

Preferably the nutritional support product is a water gel system.

Preferably the water gel system is thermostable.

Preferably the thermostable water gel system is able to withstand an extended period of residence in the rumen gut.

Preferably the water gel system includes Trehalose.

Preferably the water gel system includes a hydrocolloid and Trehalose.

Preferably the water gel system includes any one or more of kappa carrageenan, Xanthan Gum or Gum Acacia.

Preferably the water gel system includes inorganic mineral salts, attractant and other additives.

According to another aspect of the invention there is provided a composition for increasing milk production in lactating animals and/or treating/controlling infective diarrhea, the composition including between about 7-15% of gluco- and/or isomalto-oligosaccharides, 2.0-6.0% Trehalose, about 1.2-4.7% hydrocolloid, and water.

Preferably the hydrocolloid in the composition is selected from any one or more of kappa carrageenan, Gum Acacia, or Xanthan Gum.

Preferably the composition contains 1.0-3.5% kappa carrageenan, 0.2-0.7% Gum Acacia, 0-0.5% Xanthan Gum.

Preferably the composition contains excipients including any of the following inorganic mineral salts, vitamins, attractants and other additives.

Further embodiments will become apparent from the following description and drawings.

BRIEF DESCRIPTION OF THE FIGURES

The invention will now be described with reference to preferred embodiments of the invention depicted by way of example in the following figures.

DETAILED DESCRIPTION OF THE INVENTION

The benefits of increasing the health and well being of farm animals, such as ruminants, is readily apparent. Many of the health problems with such animals develop from the gut which can develop parasite loading as well as bacterial and viral infections that can result in an increased occurrence of afflictions such as infective diarrhea. Products are available to treat such afflictions but, these products are in general expensive (both in terms of the products themselves, and the labor required to administer them), invasive, and involve the use of antibiotics and/or electrolyte solutions.

The invention is broadly directed to methods and compositions for increasing the health and production of ruminant animals. In particular the invention seeks to reduce the incidence of problems such as infective diarrhea by using alternative non-invasive methods to antibiotic treatment and the like. Essentially this involves feeding the animal with gluco- and/or isomalto-oligosaccharides at an amount effective to treat or control infective diarrhea that can ultimately lead to the death of the animal.

It has been surprisingly found that oral administration of gluco- and/or isomalto-oligosaccharides to ruminants as a food or food additive composition, substantially reduces the incidence of infective diarrhea and associated health problems and substantially increases the production capability of animals. Thus the invention in another aspect can be seen to be a method of reducing the incidence of infective diarrhea by orally administering to the animal an effective amount of gluco- and/or isomalto oligosaccharides.

In particular, it has also been surprisingly found that oral administration of gluco- and/or isomalto-oligosaccharides has the effect of increasing the milk production of adult lactating cows. Thus the invention in another aspect can be seen to be a method of increasing milk production by orally administering to the animal an effective amount of gluco- and/or isomalto oligosaccharides.

Gluco-oligosaccharides and isomalto-oligosaccharides are a group of carbohydrates that resist the processes of acid and enzyme hydrolysis in the digestive tract but which are selectively fermented by mainly lactobacillus and bifidobacterium. Such gluco- and/or isomalto-oligosaccharides are together referred to in this description as "functional carbohydrates" for ease of reference.

Gut populations of microbiota include toxigenic organisms such as *Escherichia coli, Salmonella* Brandenburg (known to be associated with spontaneous abortion in sheep), pathogens like clostridia and proteolytic bacteriocides; as well as beneficial flora including bifidobacteria and lactobacillus.

Beneficial gut flora carry out saccharolytic fermentation of carbohydrates to produce short chain fatty acids which are further metabolized, or used to stimulate further growth of a limited number of colonic bacteria. Metabolic process products include vitamins and natural antibiotics. An increase in the beneficial microflora also reduces the population of harmful bacteria by a process referred to as competitive exclusion.

Proteolytic fermentation is carried out by pathogenic and toxigenic bacteria to produce mainly phenols, amines and ammonia all of which are toxic. A reduction in these bacteria by either intervention from naturally produced antibiotics or by competitive exclusion reduces the level of digestive toxins absorbed back into the body with an immediate health consequence to the animal. Non-limiting examples of such bacteria include *E coli*, ETEC, EPEC, EHEC, EIEC, *Salmonella, Salmonella* Brandenburg, *Listeria monocytogenes, Clostridium perfringens. Campylobacter, Staphylococcus aureus, Streptococcus*. Non-limiting examples of other pathogens causing complications in the animal's gut include *Rotavirus, Coronavirus, Cryptosporidia*.

The use of functional carbohydrates to increase the amount of beneficial bacteria and increasing saccharolytic fermentation in the gut is a non-invasive method of treating and regulating intestinal gut function by increasing the competitive advantages of beneficial bacteria and by using the metabolic process products of saccharolytic fermentation.

By feeding the animal functional carbohydrates, a variety of beneficial processes seem to be stimulated in the gut of the animal resulting in a treatment effect on bacterial and viral infections with a consequent reduction in fatality and an increase in animal weight gain and production to a greater extent than would be expected.

Additionally, the degradation products of saccharolytic fermentation of functional carbohydrates have a higher carbon dioxide and lower methane content in comparison to the fermentation of other kinds of carbohydrate (such as fructo-oligosaccharide). This reduction in methane emission is beneficial for the environment.

It has been reported that feeding ruminant animals the functional carbohydrates reduced the worm count thus allowing a reduction in drenching requirements (see Example 5). An effect of the method and composition of the invention appears to be a reduced parasite loading.

The use of the present invention seems to have a prophylactic effect to reduce the ability of harmful bacteria (e.g. *Salmonella* Brandenburg) from taking hold in the digestive tract of the animal. The incidence of *Salmonella* Brandenburg outbreaks is sporadic, but on the increase in New Zealand. The prophylactic effect may be shown minimize the effects of *Salmonella* Brandenburg on birth rates in sheep, thereby at least maintaining standard birth rates of flocks exposed to *Salmonella* Brandenburg infection. The animals could be fed the functional carbohydrate as part of an ongoing diet to increase production of the animal and its overall health, rather than simply as a treatment for animals exhibiting symptoms of infective diarrhea. With the increased gut health of the animal, it may also be that a reduction in fly strike as a result of decreased scouring (infective diarrhea) could also occur.

Preferably the functional carbohydrates will be administered to the animal at about 2 to 60 grams of carbohydrate per day although more could be used if available and desired. Higher amounts are likely to undesirably stimulate intestinal motility in the animals however. It is more preferred to use between about 5-30 or about 10-30 grams. For bovine animals a preferred range is between about 10-30 grams, more preferably about 15-25 grams and for the ovine between about 2-20 grams, more preferably about 5-10 grams with lambs the amount administered can be as low as 1 gram per animal per day, although 2 grams is preferred. Administration can be achieved by mixing the functional carbohydrate into stock food or other nutritional support products such as reconstituted milk, milk replacer, water, fortified water, electrolyte solutions, water gels or blended powders at an amount of about 150 to 5000 ppm. It is more preferable to use between about 300 and 5000 ppm or about 300 and 1000 ppm. The total composition is then administered to the animal in an amount per day to meet the preferred administration amount. To this extent the invention could be seen to be a food or food additive. As will be readily apparent, if the user desired to use natural treatments, a focus on milk and similar support products could be used. A variety of alternatives would be well known to the skilled person. Alternative forms of administration would include formulated drenches and like means as would be known to the skilled person.

The functional carbohydrates may be administered via a water gel system which acts as the nutritional support. This water gel system will preferably include a carrier system that includes kappa carrageenan, Xanthan Gum, konjac, chitosan and/or locust bean gum dispersed into a water phase containing the oligosaccharide. Other ingredients could include Trehalose, Gum Acacia, inorganic mineral salts, attractants and other additives or actives. The inorganic mineral salts can include Magnesium or Zinc salts to treat the staggers and facial eczema, or potassium and/or sodium salts as an electrolyte for animals grazed in hot conditions.

The combination of Xanthan gum, carrageenan and konjac provides a thermally stable, economic system that allows for a longer period of resistance in the gut of calves, sheep and deer. Longer residence time allows for staged or delayed release of the functional carbohydrates to the animal. It also provides a method of delivery to animals grazed in remote areas, and animals that drink from natural reservoirs. The thermostability also allows functional carbohydrates to be delivered to areas of high temperature, e.g. New Zealand high country, or milking sheds, without damage to the ingredients in the water gel system.

An alternative and preferred, combination would include the use of Trehalose, together with other ingredients, including hydrocolloids such as Xanthan Gum, Gum Acacia, and kappa carrageenan. This would maintain the stability benefits of the composition but, due to the use of Trehalose, water loss will be reduced as will be the formation of ice crystals in cold weather.

A preferred composition for this is set out in Table 1 below.

TABLE 1

| Ingredient | Amount required |
|---|---|
| Kappa Carrageenan | 1.0-3.5% |
| Xanthan Gum | 0-0.5% |
| Gum Acacia | 0.2-0.7% |
| Trehalose | 2.0-6.0% |
| Glucidex 6 | 7.0-15.0% |
| Water distilled | 65-89% |
| Colour/Attractants | q.s. |
| Inorganic Mineral salts | q.s. (according to seasonal requirements) |

The functional carbohydrates (as defined earlier) of use in the present invention are the indigestible oligosaccharides, gluco- and/or isomalto-oligosaccharides. As will be apparent to the skilled person, a number of other carbohydrates will also fall within the definition of an indigestible oligosaccharide. It is, however, known that other oligosaccharides have undesirable traits for use in ruminant animals. For example, fructo-oligosaccharide contains a natural level of sweetness that may be unpalatable and can lead to an increased production of gas that is not desirable for the rumen gut. As a result, it is likely that the beneficial effects described herein may not be observed. The preferred composition of use in the method and compositions of the present invention will include gluco-oligosaccharides, or isomalto-oligosaccharides or a mixture of the two. While other oligosaccharides may be present as a result of the fermentation and hydrolysis processes used to prepare the oligosaccharides, these other oligosaccharides will be present in insignificant amounts of less than about 0.2% of the total oligosaccharide.

Most preferably gluco-oligosaccharides are used by themselves or will comprise the major part of a gluco/isomalto oligosaccharide mixture. Isomalto-oligosaccharides are usually sourced in a powder form, which tends to be hydrophilic in nature, and is therefore difficult to store. Alternatively the isomalto-oligosaccharides can be sourced as a 50% syrup, which increases the purchase and storage costs. The gluco-oligosaccharides can be sourced as a powder which is easier to use and store, and therefore tends to be more cost effective. A source of gluco-oligosaccharide, as listed in Table 1 above, is Glucidex 6.

The effect of the administration of functional carbohydrates on milk production is marked but the reason for it is unclear. It may simply be a function of improved health in the animals, but it does not seem that this alone would account for the production increases shown (see Example 3-Table 4). The results are not clearly derived from simply the observed effects on infective diarrhea and the gut microflora of the animal.

It is possible that gluco-oligosaccharides will be the only oligosaccharide that produces the effect on lactation as this forms the major part of the oligosaccharides administered to the animal. It is also possible that isomalto-oligosaccharide alone will work but further work will be required to confirm this.

EXAMPLES

Example 1

Bovine Calf Initial Trials

Random groups of new born bovines were selected to provide a cross population of animals likely to be exposed to a range of infection risk. Gluco-oligosaccharide ("GOS") at an amount of 20 g per day was included in food regimes and the animals monitored for signs of infective diarrhea. A control group study without the added gluco-oligosaccharide in the food regime was also similarly monitored.

The study of newborn calves was to determine if enteral dosing would reduce the occurrence of diarrhea. An increase in the rate of survival of the study population would be an outcome and improved weight gain of the animals a term result The results are reported in Table 2.

TABLE 2

| | Group 1 | Control 1 | Group 2 | Control 2 |
|---|---|---|---|---|
| Number of calves | 75 | 115 | 180 | 180 |
| Age of calves | +4 days | +4 days | +4 days | +4 days |
| Dosage rate | 20 g/day | Nil | 30 g/day | Nil |
| Number of calves with diarrhea | 7/9.3% | 55/47.8% | 2/1.1% | 22/12.2% |
| Fatalities | 2/2.6% | 13/11.3% | 1/0.6% | 5/2.8% |

The calves in the Group 1 study were housed in covered calf pens with strawed floor and fed from mechanical feeding stations with a calf milk replacer to which the gluco oligosaccharide was separately added in a dispersed solution.

At the onset of diarrhea the affected calf was dosed with an electrolyte solution to prevent unnecessary fatality and recorded as a diarrhea event. The feeding regime was not altered.

The results of the study indicate that dosing calves with gluco-oligosaccharide is effective in reducing the incidence of infective diarrhea. The reduction in incidence of diarrhea from 47.8% to the 9.3% is considered significant and indicates the beneficial effect of the treatment regime. In addition, the reduction In fatality from 11.5% to 2.6% is also significant.

The results of the Group 2 study confirm that significant reductions in both diarrhea and fatality rates were observed and support the conclusions drawn from the first study group.

Example 2

Bovine Calf Field Trials

A group of 15 farms comprising a mix of calf rearers, dairy farmers and dairy beef farmers were supplied with an oligosaccharide composition consisting of enzymatically hydrolysed dextrin including approximately between 1.5 and 3% of the total mixture as isomalto-oligosaccharide and the remainder largely gluco-oligosaccharide, as described by the properties set out in Table 3.

TABLE 3

| Property | Characteristic | |
|---|---|---|
| Dextrose Equivalent | 50 | |
| Degree of Polymerisation | DP1 | 0.2% |
| | DP2 | 0.8% |
| | DP 3 | 1.5% |
| | DP 4 | 1.7% |
| | DP 5 | 1.8% |
| | DP 6 | 2.3% |
| | DP 7 | 2.7% |
| | DP 8 | 2.3% |
| | DP 9 | 1.9% |
| | DP10-20 | 27.9% |
| | DP > 20 | 57% |

TABLE 3-continued

| Property | Characteristic |
| --- | --- |
| Molecular Weight | >5000-6000 |
| Alcohol Insoluble Fibres % DS | <20 |
| % Glucosidic Linkages | (1-4) 50-64 |
|  | (1-6) 20-25 |
|  | (1-2) 7-10 |
|  | (1-3) 9-11 |
| Glucose % | 0.5% |
| Maltose | 1.0% |
| Oligo/Poly | 98.5% |

The farms were in diverse locations to provide a random cross section of conditions. A total number of 2963 calves were monitored. The feeding of newborn calves remains a universally similar method in the first few weeks of life.

A group of 5 farms was established as non user sites, totaling 1030 calves and also in diverse locations to provide a random profile.

The trial period commenced on 1 Jul. 2002 and concluded on 29 Sep. 2002. The oligosaccharide composition was added to calf milk or calf milk replacer at the user sites at the rate of 20 grams per calf daily. This was continued until the calf was weaned from milk feeding.

The number of calves either born or received onto each farm was recorded in each week and multiplied by seven to give Calfdays, a representation of the number of days of monitoring per calf. The number of calves that were observed and treated for scouring was also recorded and the days that each calf scoured for also recorded (Scourdays). Calf fatalities were also recorded but the cause of death not specifically isolated in all cases. This proved to be impractical in the field as it requires veterinary autopsy.

This provided a comparative data base in each group of users and non users of total calf days for the period and the total number of scour days.

Figure 1:
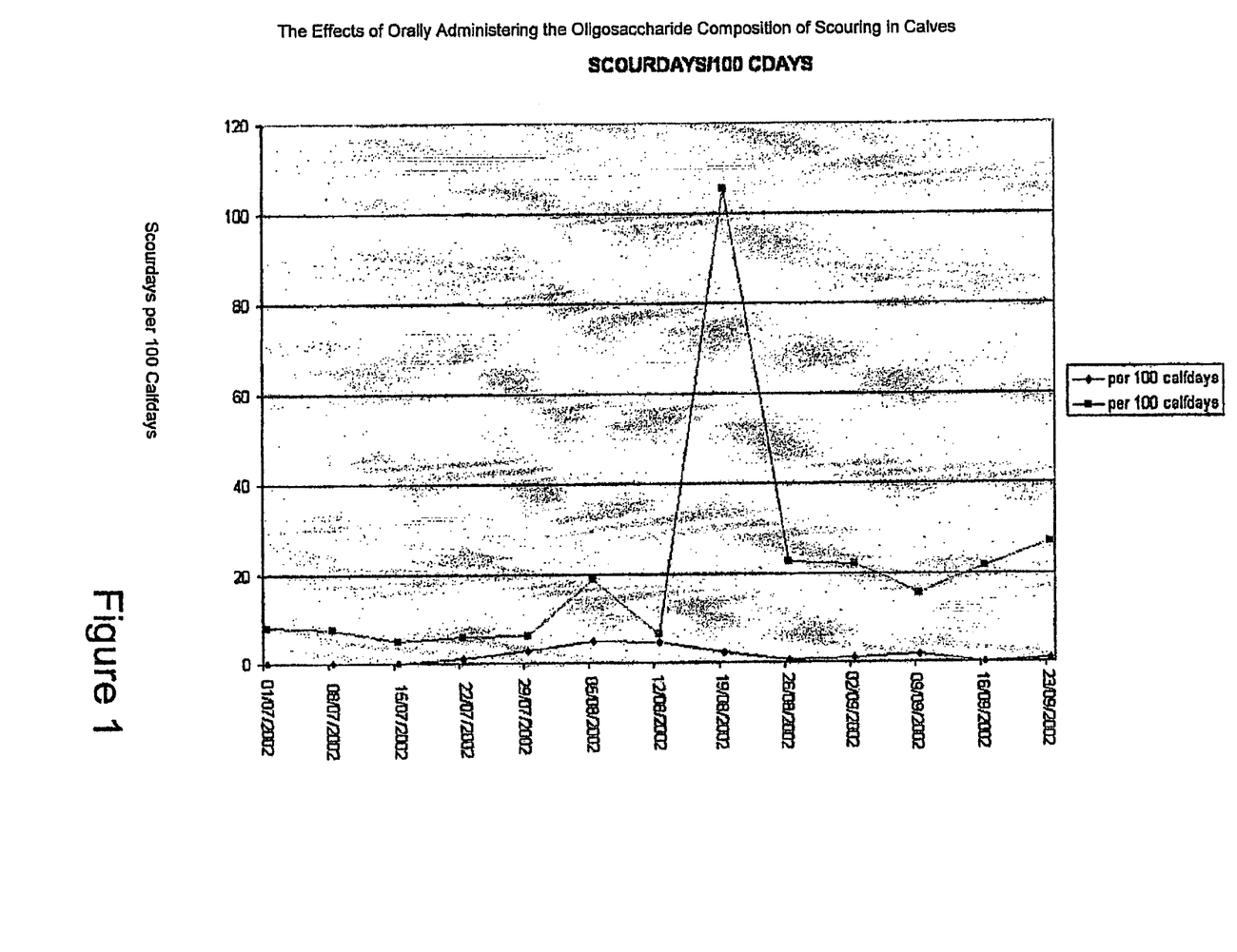
FIG. 1: A graph showing the incidence of scouring in calves that were orally administered a preferred composition as described herein, in comparison to control calves.

The results which are plotted in FIG. 1 show a clear reduction in the rate of scouring in the calf population that was treated with the oligosaccharide composition. In cases where infective scouring occurred in the treated population the effects were much less severe and recovery rates were quicker. Calf fatality rates in the non treated group were significantly higher for the infected animals.

The results show a consistently lower rate of scouring in the treated group which for the first three weeks record a zero result whilst infection in the control group is present from the outset.

During the week of 19 Aug. 2002 there was a rapid increase in the scour rate of the control group as a result of an outbreak of rotavirus on two farms. These farms were located geographically far apart. The treated group recorded an increase in scour rates in the prior 2 weeks of 5 and 12 Aug. 2002 but at much lower rates. Rotavirus is reported as a common affliction in calves in the August month. There is the likelihood of a favorable environment for infection due to seasonal change in this month. The data reflects this.

The rate of infection of the treated group for the whole period is 2.29 scourdays per 100 calfdays whilst in the control group the rate is 16.82 scourdays per 100 calfdays. This is an effective rate of 7.34 times the rate of infection in the control group over the treated group.

The user group is a wider base in number and site than the control but the probability of an adverse result appearing is much greater in a wider group. There is little or no predictability in result in either groups as the calves are newborn, site selection having taken place prior to the calving season.

Calves suffer from infective diarrhea from three basic causes, bacteriological, viral and nutritional. Calves that suffer from high stress immediately post birth are also likely to scour. The reasons are traceable often to transport to and from saleyards shortly after birth, exposure to virus and bacteria in saleyard environments, inadequate supply of colostrum immediately after birth or protein overload from protein rich feed.

The data indicates strongly that the administration of the oligosaccharide composition of the present invention in the diet of the animal alleviates or mitigates the adverse effect of infective diarrhea in newborn calves.

Example 3

Bovine Lactating Adult Initial Trials

Random groups of adult bovines were selected to provide a cross population of animals likely to be exposed to a range of infection risk. Gluco-oligosaccharide ("GOS") at an amount of 20 g per day was included in food regimes and the animals monitored for signs of infective diarrhea. A control group study without the added gluco-oligosaccharide in the food regime was also similarly monitored.

The study of adult lactating cows was to determine if enteral dosing with functional carbohydrate would improve milk yield per animal as a consequence of increased digestive function and reduced infective diarrhea. Functional carbohydrate as used in Example 1 was given to the cows in group 1 by direct drenching. Functional carbohydrate as used in Example 1 was given to the cows in group 2 by addition to the cows' water supply using a Dosetron system. Daily milk production per animal measured for each group. The results are reported in Table 4.

TABLE 4

|  |  | Group 1 | Control 1 | Group 2 | Control 2 |
| --- | --- | --- | --- | --- | --- |
| Number of cows |  | 101 | 246 | 262 | 262 |
| Dosage/cow | GOS | 10 g/day | Nil | 10 g/day | nil |
| Milk yield per cow. Average litres/day | Pre | 1561 | 3640 | 4188 | 4213 |
|  | During | 1646 | 3735 | 4506 | 4339 |
|  |  | +5.4% | +2.6% | +7.6% | +3.0% |
| Milk Fat % | Pre | 4.84 | 4.63 | 4.22 | 4.20 |
|  | During | 5.02 | 4.68 | 4.65 | 4.33 |
|  |  | +3.7% | +1.1% | +10.2% | +3.1% |
| Total Protein | Pre | 3.43 | 3.52 | 3.42 | 3.42 |
|  | During | 3.98 | 3.68 | 3.77 | 3.51 |
|  |  | +16.0% | +4.5% | +10.2% | +2.6% |
| Faecal Appearance | Pre | Loose | Loose | Loose | Loose |
|  | During | Firm at day 6 | Loose/firm | Firm at day 10 | Loose at day 14 |

The trials were conducted at a time when pasture feed remained of a consistent nature. Defecation was monitored as an indicator of digestive differences or change between the control and study group.

The results of the study indicate that feeding functional carbohydrate to cows increases milk production, improves digestive function and reduces infective diarrhea. In particular the percentage increase of milk production per cow and the percentage increase of milk fat in the milk produced is significant and offer economic benefits to farmers using the functional carbohydrates as a food supplement.

Example 4

Bovine Lactating Adult Field Trials

A trial herd of 440 milking cows (noted as TRD) was orally administered 15 grams of the oligosaccharide composition as described in Example 2, in a solution of water by metered drench gun daily over the period of the study. The daily yield of the herd for milk volume, milk fat and protein was recorded and plotted. Intervention points were included in the trial to assess if natural production would alter if the treatment was discontinued and restarted.

An averaged profile of 8 other herds totaling 1772 cows was also established comprising the following

TABLE 5

| Herd A | 160 |
|---|---|
| Herd B | 200 |
| Herd C | 192 |
| Herd D | 334 |
| Herd E | 230 |
| Herd F | 186 |
| Herd G | 280 |
| Herd H | 190 |
| Total: | 1772 |

The daily yields of these herds was also recorded and averaged to 440. The results were plotted to provide a control performance profile (see FIGS. 2, 3 and 4).

All the herds are located In the same geographic region. Environmental and pasture differences were as far as possible minimized. No changes were made to the normal farming management of the herds.

The trial commenced on 01 Jan. 2002. The trial herd performance against the average profile was recorded for 43 days without dosing with the composition described in Example 2. On 13 Feb. 2002 dosing of the trial herd commenced. Daily production data was recorded from 1 Jan. 2002 to 15 May 2002 for both trial herd and the control herds.

Dosage of the trial animals commenced on 13 Feb. 2002 and continued on a daily basis until 8 Mar. 2002 when dosing was stopped for a short period. Dosing was recommenced on 22 Mar. 2002 and continued until the herds were dried off.

Figure 2:
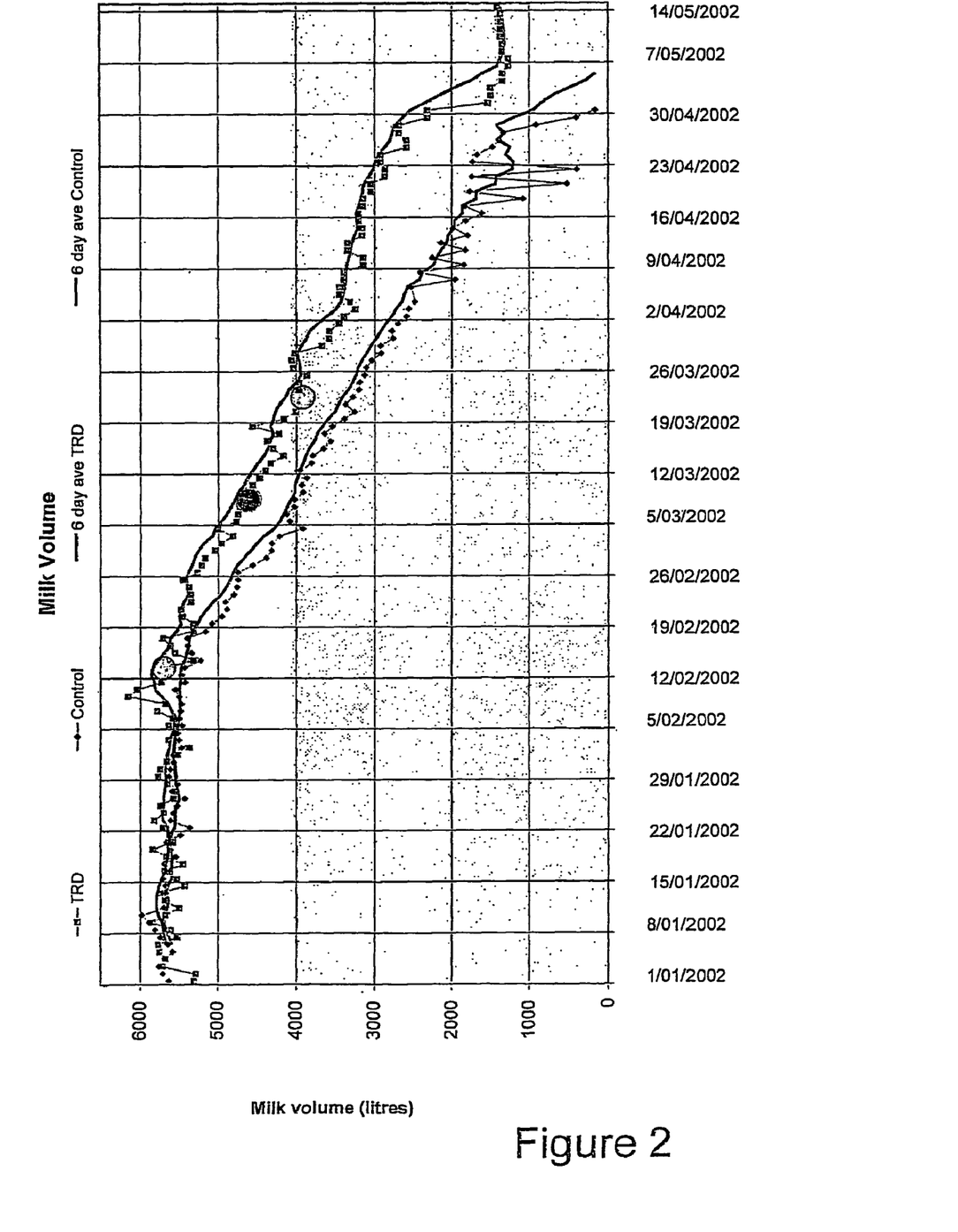
FIG. 2: A graph showing the milk volume produced by bovine animals that were orally administered a preferred composition as described herein, in comparison to control bovine animals.
Figure 3:
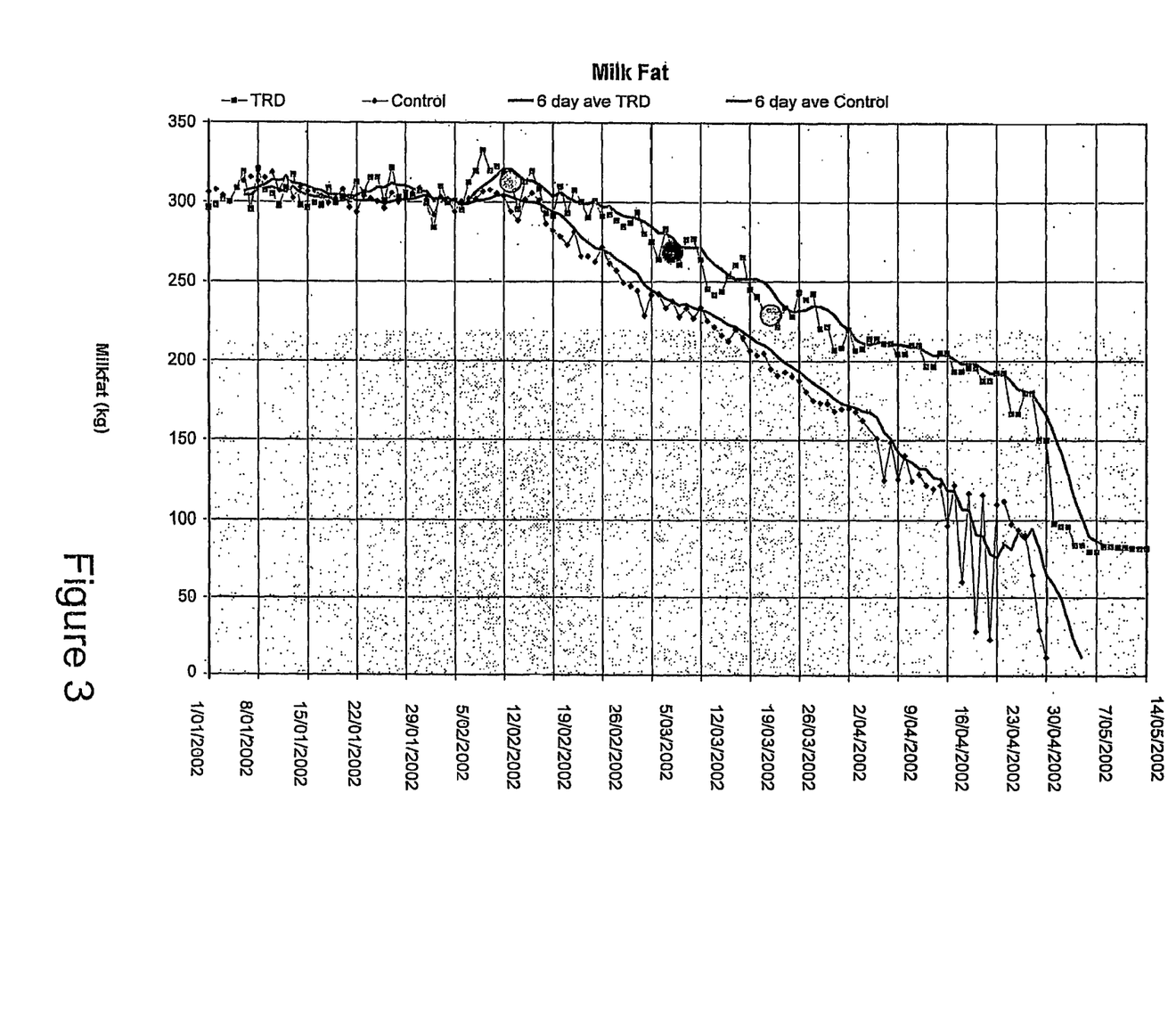
FIG. 3: A graph showing the total milk fat in milk produced by bovine animals that were orally administered a preferred composition as described herein, in comparison to control bovine animals.
Figure 4:
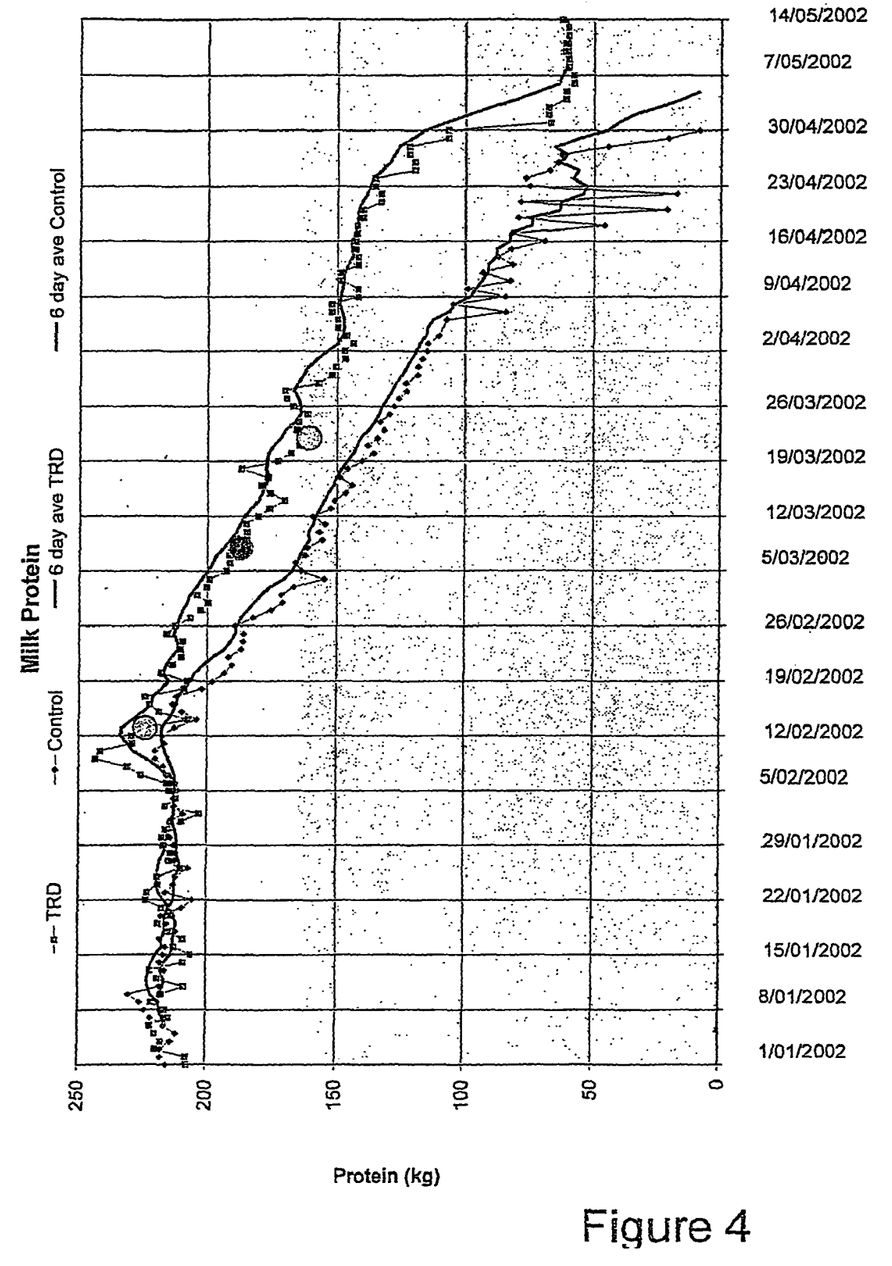
FIG. 4: A graph showing the total milk protein in milk produced by bovine animals that were orally administered a preferred composition as described herein, in comparison to control bovine animals.

With reference to FIGS. 2, 3 and 4, in the pretrial period 1 Jan. 2002-5 Feb. 2002 there is no significant difference to be seen in milk volume, milk fat or protein content between the control herd profile and that of the trial herd (TRD). This indicates that despite differences in location, possibly feed composition and farm practice, there is little difference in the outcomes of natural production between the herds. The averaged control herd profile can be seen as a reliable guide to performance.

Shortly after the commencement of dosing on 13 Feb. 2002, with the composition described in Example 2, a significant trend begins to appear in the production data for the three component items—volume, fat and protein. This also is observed on recommencement of dosing at 22 Mar. 2002.

The differences in total milk volume, fat and protein contents recorded at various time intervals are entered in the Tables 6, 7 and 8, and indicate similar differences in superior production of the dosed herd.

TABLE 6

Comparison of Total Milk Volume (Litres) between dosed and non-dosed herds.

| Date | No dosing (Control) | Dosed | Difference (%) |
|---|---|---|---|
| 05 Mar. 02 | 4082 | 4760 | +678 (16.6%) |
| From 15 Feb. 2002 to: 05 Mar. 02 | 98056 | 109670 | +11615 (11.8%) |
| From 15 Feb. 2002 to: 07 May 02 | 228970 | 310820 | +81850 (35.7%) |

TABLE 7

Comparison of Total Milk Fat (kg) between dosed and non-dosed herds.

| Date | No dosing (Control) | Dosed | Difference (%) |
|---|---|---|---|
| 05 Mar. 02 | 242 | 275 | +33.3 (13.7%) |
| From 15 Feb. 2002 to: 05 Mar. 02 | 5579 | 6169 | +590 (10.6%) |
| From 15 Feb. 2002 to: 07 May 02 | 13628 | 18497 | +4869 (35.7%) |

TABLE 8

Comparison of Total Milk Protein (kg) between dosed and non-dosed herds.

| Date | No dosing (Control) | Dosed | Difference (%) |
|---|---|---|---|
| 05 Mar. 02 | 164 | 193 | +29.2 (17.8%) |
| From 15 Feb. 2002 to: 05 Mar. 02 | 3871 | 4361 | +490 (12.7%) |
| From 15 Feb. 2002 to: 07 May 02 | 9398 | 13044 | +3646 (38.7%) |

During the period of the trial there would have been a natural decline in the feed value of pasture. This is a natural phenomenon and it appears that increased efficacy in digestive function by dosing with the composition of the present invention modulates gut flora in the animals enabling better absorption of the available nutrients from pasture than would otherwise occur. The trial data supports this contention. The difference between the herds toward the end of the season is marked.

The trial data indicates that when dosing was discontinued at 8 Mar. 2002 that the production indicators trend back to the control profile and, at recommencement, on 22 Mar. 2002, there is an upward trend in performance.

Example 5

Parasite Loading in Ovine Animals.

Following weaning, a flock of lambs were orally administered 2 g per day per animal of the composition described in Example 2 via a water trough. The lambs were then monitored for parasitic infection and growth and these observations are recorded in Table 9.

TABLE 9

| Date | Worm Count | Comments |
| --- | --- | --- |
| 10 Jan. 2002 | | Weaned and drenched |
| 04 Feb. 2002 | | Drenched - oligosaccharide composition started in feeding regime |
| 18 Feb. 2002 | Zero | |
| 25 Feb. 2002 | 15 | |
| 03 Mar. 2002 | Zero | |
| 19 Mar. 2002 | 125 | |
| 25 Mar. 2002 | 150 | Average weight = 38.6 kg |
| 26 Mar. 2002 | | Drenched |
| 08 May 2002 | | Drenched Average weight = 41 kg (5 kg heavier than usual at this age) Lambs go onto swedes |
| 12 Jun. 2002 | 300 | Drenched |
| 05 Aug. 2002 | 60 | |
| 28 Aug. 2002 | 90 | Shorn |
| 21 Sep. 2002 | Zero | |

Traditional farming practices mean that the lambs would usually be drenched every three weeks from weaning through until May/June 2002. The decreased parasite loading shown in these lambs meant that the number of drenches required in this time was cut down from the usual number of 7 to 5. A worm count of 300-400 is usually the trigger for drenching. In this flock, a more conservative worm count of 200-300 is used as the trigger. Using the more traditional trigger levels of 300-400. The number of drenches could have been further reduced to 4.

There are trends apparent from the observation of this flock, that the use of the oligosaccharide composition appears to be beneficial for reducing parasite loading (and the associated costs and labor of drenching) and for improving the general health and weight of the lambs. More evidence is required to determine the mechanism behind this apparent benefit of using the oligosaccharide composition however it is suspected that the general improvement of gut health in the animals that are being administered the oligosaccharides will be a key factor.

Example 6

Preferred Water-Gel Composition

The water gel tablet is made in the following way: 0.1 grams of Xanthan Gum, 0.2 grams of Acacia Gum, 2.0 grams of Trehalose (Hayashibara Treha) and 10 grams of Glucidex 6 (Roquette Freres) is dissolved in water. 1.2 grams of kappa carrageenan (FMC Gelcarin GP911) is dissolved into the solution and then the solution is heated to 65° C. while maintaining a slow agitation. The temperature is then reduced to 25° C. At this point, a mineral premix and other optional additives may be added to the mixture if required.

The mixture, now viscous, is passed through a sized aperture and dropped into a chilled water bath containing 15% potassium chloride. The formed gel tablets are removed from the potassium chloride solution and passed over a cold air column and then coated in a dry polyol such as sorbitol powder.

The tablet formed is thermostable and has good resistance to water loss and ice crystal formation.

The foregoing describes the invention including preferred forms thereof. Alterations and modifications that would be obvious to the skilled person are intended to fall within the scope of the invention as disclosed and claimed.

What is claimed is:

1. A method of increasing milk production in bovine animals, the method including a step of orally administering to an adult lactating bovine animal a composition containing an effective amount of an indigestible oligosaccharide, wherein the indigestible oligosaccharide is (a) a gluco-oligosaccharide; or (b) a mixture including a gluco-oligosaccharide and an isomalto-oligosaccharide, thereby increasing the milk production in said adult lactating bovine animal.

2. The method according to claim 1 wherein the indigestible oligosaccharide is carried in a nutritional support product.

3. The method according to claim 2 wherein the nutritional support product contains conventional additives and/or excipients including inorganic salts, minerals, and attractants.

4. The method according to claim 2 wherein the nutritional support product is a water gel system.

5. The method according to claim 4 wherein the water gel system is thermostable.

6. The method according to claim 1 wherein the amount of indigestible oligosaccharide is administered to the adult lactating bovine animal at a daily rate of between about 2-60 grams.

7. The method according to claim 1 wherein the amount of indigestible oligosaccharide is administered to the adult lactating bovine animal at a daily rate of about 10-30 grams.

8. The method according to claim 2 wherein the indigestible oligosaccharide is present in the nutritional support product in an amount of between about 150-5000 ppm.

9. The method according to claim 1 wherein the composition includes a nutritional support product and between about 150 and 5000 ppm of an indigestible oligosaccharide.

10. The method according to claim 4 wherein the water gel system includes Trehalose and a hydrocolloid.

11. The method according to claim 1 wherein the composition includes between about 7-15% of (a) a gluco-oligosaccharide; or (b) a mixture including a gluco-oligosaccharide and an isomalto-oligosaccharide, wherein the composition further comprises about 2.0-6% trehalose, about 1.2-4.7% hydrocolloid, and water.

12. The method according to claim 11 wherein the hydrocolloid in the composition contains about 1.0-3.5% kappa carrageenan, about 0.2-0.7% Gum Acacia and about 0-0.5% Xanthan Gum.

13. The method according to claim 11 wherein the composition further contains excipients selected from any of the following: inorganic mineral salts, vitamins, and attractants.

14. The method according to claim 2 wherein the nutritional support product is one selected from the group of milk, reconstituted milk, milk replacer, water, fortified water, electrolyte solutions, water gels, and blended powders.

* * * * *

UNITED STATES PATENT AND TRADEMARK OFFICE
CERTIFICATE OF CORRECTION

| | |
|---|---|
| PATENT NO. | : 7,956,045 B2 |
| APPLICATION NO. | : 10/497291 |
| DATED | : June 7, 2011 |
| INVENTOR(S) | : Lane |

It is certified that error appears in the above-identified patent and that said Letters Patent is hereby corrected as shown below:

In Table 3, at line 57 of column 8 of the patent

Dextrose Equivalent       50

Delete the number "50" and insert -- 5 --.

Signed and Sealed this
Thirteenth Day of September, 2011

David J. Kappos
*Director of the United States Patent and Trademark Office*